(12) United States Patent
Kallio et al.

(10) Patent No.: US 10,095,265 B2
(45) Date of Patent: Oct. 9, 2018

(54) ADAPTABLE MICROCONTROLLER-OPERATED DEVICE AND RELATED SYSTEM

(71) Applicants: Janne Kallio, Vantaa (FI); Erik Lindman, Vantaa (FI); Mikko Martikka, Vantaa (FI); Kimmo Pernu, Vantaa (FI)

(72) Inventors: Janne Kallio, Vantaa (FI); Erik Lindman, Vantaa (FI); Mikko Martikka, Vantaa (FI); Kimmo Pernu, Vantaa (FI)

(73) Assignee: Amer Sports Digital Services Oy, Vantaa (FI)

( * ) Notice: Subject to any disclaimer, the term of this patent is extended or adjusted under 35 U.S.C. 154(b) by 879 days.

(21) Appl. No.: 13/691,876

(22) Filed: Dec. 3, 2012

(65) Prior Publication Data

US 2013/0339409 A1 Dec. 19, 2013

Related U.S. Application Data

(60) Provisional application No. 61/649,632, filed on May 21, 2012.

(30) Foreign Application Priority Data

Dec. 5, 2011 (FI) .................................. 20116231

(51) Int. Cl.
*G06F 15/00* (2006.01)
*G06F 1/16* (2006.01)
(Continued)

(52) U.S. Cl.
CPC ............ *G06F 1/163* (2013.01); *A61B 5/0205* (2013.01); *A61B 5/02055* (2013.01);
(Continued)

(58) Field of Classification Search
CPC .... G04G 17/08; G04G 21/04; G06F 19/3481; G06F 1/163; G06F 3/048
See application file for complete search history.

(56) References Cited

U.S. PATENT DOCUMENTS

| 5,197,489 A | 3/1993 | Conlan |
|---|---|---|
| 5,603,021 A | 2/1997 | Spencer et al. |

(Continued)

FOREIGN PATENT DOCUMENTS

| CH | 698848 B1 | 11/2009 |
|---|---|---|
| CN | 1366417 A | 8/2002 |

(Continued)

OTHER PUBLICATIONS

LabVIEW Tutorial Manual [online], Jan. 1996, National Instruments Corporation. Retrieved from the Internet: <URL: www.ni.com/pdf/manuals/320998a.pdf> [retrieved on Dec. 6, 2012].

(Continued)

*Primary Examiner* — Elias Desta
(74) *Attorney, Agent, or Firm* — Seppo Laine Oy

(57) ABSTRACT

The invention concerns a portable computing device comprising a microprocessor capable of running software, hardware means capable of providing at least one physical variable, a memory unit carrying the software adapted to read the physical variable and to perform a mathematical operation utilizing the physical variable. An interface means adapted to allow defining of the mathematical operation in the memory unit by a user of the device. The invention also concerns a firmware product of a microcontroller-operated device, a computer program product and a web service.

27 Claims, 2 Drawing Sheets

(51) Int. Cl.
*A61B 5/0205* (2006.01)
*A61B 5/00* (2006.01)
*A61B 5/11* (2006.01)

(52) U.S. Cl.
CPC ............. *A61B 5/681* (2013.01); *A61B 5/1122* (2013.01); *A61B 2560/0242* (2013.01)

(56) References Cited

U.S. PATENT DOCUMENTS

| | | | |
|---|---|---|---|
| 5,899,204 A | 5/1999 | Cochran | |
| 6,556,222 B1 | 4/2003 | Narayanaswami | |
| 7,310,549 B1 | 12/2007 | Angelini et al. | |
| 7,905,026 B2 | 3/2011 | Martikka et al. | |
| 8,021,306 B2 | 9/2011 | Martikka et al. | |
| 8,292,820 B2 | 10/2012 | Punkka et al. | |
| 9,297,650 B2 * | 3/2016 | Nieminen | G01C 25/00 |
| 2004/0057340 A1 | 3/2004 | Charles-Erickson et al. | |
| 2005/0038332 A1 | 2/2005 | Saidara et al. | |
| 2005/0282650 A1 | 12/2005 | Miettinen et al. | |
| 2005/0283313 A1 | 12/2005 | Kaltto et al. | |
| 2006/0009261 A1 | 1/2006 | Ruotsalainen et al. | |
| 2006/0100753 A1 * | 5/2006 | Katzer | A63H 19/24 701/20 |
| 2006/0167784 A1 * | 7/2006 | Hoffberg | G06Q 20/401 705/37 |
| 2006/0190413 A1 | 8/2006 | Harper | |
| 2007/0094642 A1 | 4/2007 | Dove et al. | |
| 2007/0283953 A1 | 12/2007 | Angelini et al. | |
| 2008/0167536 A1 | 7/2008 | Teller et al. | |
| 2008/0172450 A1 | 7/2008 | Wu et al. | |
| 2008/0255432 A1 | 10/2008 | Nielsen et al. | |
| 2010/0210975 A1 | 8/2010 | Anthony, III et al. | |
| 2010/0250208 A1 | 9/2010 | Leskela et al. | |
| 2010/0299073 A1 | 11/2010 | Metzler et al. | |
| 2011/0263993 A1 | 10/2011 | Martikka et al. | |
| 2012/0083705 A1 | 4/2012 | Yuen et al. | |
| 2012/0313768 A1 * | 12/2012 | Campbell | B60R 25/2009 340/438 |

FOREIGN PATENT DOCUMENTS

| | | |
|---|---|---|
| CN | 101087334 A | 12/2007 |
| CN | 101207864 A | 6/2008 |
| CN | 101419485 A | 4/2009 |
| CN | 101477636 A | 7/2009 |
| JP | 2000293778 A | 10/2000 |
| JP | 2002329008 A | 11/2002 |
| WO | 02067449 A2 | 8/2002 |
| WO | WO 2009076383 A2 | 6/2009 |

OTHER PUBLICATIONS

Akiyama et al: An on-site programming enviroment considering user contexts for wearable computing. DICOMO 2010, Series vol. 2010, No. 1, Jul. 7, 2010, pp. 1992-2000.

Wikipedia: Mikrocontroller. Nov. 10, 2011. pp. 1-6.

* cited by examiner

ADAPTABLE MICROCONTROLLER-OPERATED DEVICE AND RELATED SYSTEM

RELATED APPLICATIONS

The present application claims priority to U.S. Provisional Patent Application Ser. No. 61/649,632 titled ADAPTABLE MICROCONTROLLER-OPERATED DEVICE AND RELATED SYSTEM AND SOFTWARE PRODUCTS, and filed on May 21, 2012, and claims priority under 35 U.S.C. § 119 to Finnish Patent Application Serial No. 20116231 filed on Dec. 5, 2011.

BACKGROUND OF THE INVENTION

The invention relates to portable personal electronic devices. In particular, the invention relates to small microcontroller-operated devices, such as wrist-top computers which can be used for monitoring and/or tracking sports exercises. In particular, the invention relates to improving the adaptability of wrist-top computers.

User experience of wrist-top computers can be improved by adapting their display or graphical user interfaces to the needs of an individual user. Adaptable user interface of a diving computer is known from for example from U.S. Pat. No. 5,845,235. In addition to user interface, also the connectivity of the wrist-top computer has an effect on the user experience. U.S. Patent Application Publication No. 2010/0130123 discloses a diving computer which can communicate with another diving computer or a computer. U.S. Patent Application Publication No. 2010/0250208 disclose diving computer which is able to form a data link to receive data on available gases.

As to the information content provided to the user, the functionalities of the prior art devices are, however, relatively limited.

SUMMARY OF THE INVENTION

It is an aim of the invention to provide a wrist-top computer with improved functionality with respect to information content available to the user.

It is also an aim to provide software products and a computerized system for functionalization of wrist-top computers.

The invention is based on the idea of allowing users to define operations in relation to data provided by physical sensors or other data-producing units in or connected to a wrist-top computer. The operations can be run in real time in the device and their results may be communicated to the user. The operations or the results can also be shared with other users of the same or similar kind of device.

According to one aspect, the invention provides a portable microcontroller-operated computing device including a memory, a microcontroller, software, hardware, and an interface. The microcontroller is capable of running software stored on the memory. The hardware is capable of providing at least one physical variable. The software is adapted to read the physical variable using the hardware and to perform a mathematical operation utilizing the physical variable. The interface is adapted to allow defining of the mathematical operation in the memory by a user of the device.

In other words, the interface means is adapted to allow a user of the device to define the mathematical operation in the memory unit.

According to one embodiment, the portable microcontroller-operated computing device is a wrist-top computer.

According to another embodiment, the portable computing device is a displayless unit comprising means for wirelessly transmitting the result of the mathematical operation utilizing the physical variable to a portable host device, such as a wrist-top computer or mobile phone. For example, the device may be a foot pod or satellite positioning pod adapted to operate in functional connection with the host device. The unit may comprise integral means for measuring the physical variable.

According to one embodiment, the device is based on a single-chip microcontroller (MCU), comprising integral microprocessor core, memory, and optionally also input/output (I/O) unit(s), in contrast to devices having separate microprocessor and memory (and I/O) circuits, like portable computers and mobile phones. Such devices are called single-chip microcontroller-operated devices herein. In such devices, at least part of the basic software of the device (firmware) and/or user-defined mathematical operations can be stored in the integral memory unit.

According to one embodiment, the device comprises, in addition to or instead of the memory unit integral to the microcontroller, a memory unit external to the microcontroller. At least part of the basic software of the device (firmware) and/or user-defined mathematical operations can be stored in the external memory unit. According to one embodiment, the firmware and the mathematical operations are stored on different physical memory units. According to one example, the firmware is stored in the internal memory of the microcontroller and the mathematical operations in a memory chip external of the microcontroller.

According to one embodiment, the mathematical operation is defined in a memory portion of the memory means and the wrist-top computer comprises means for changing data on the memory portion for changing the mathematical operation.

According to one embodiment, the at least one physical variable comprises a variable descriptive of a position or movement of the wrist-top computer and the variable is provided by a sensor. The sensor may be integrally arranged in the wrist-top computer or arranged in an external unit which is in communication connection with the wrist-top computer.

According to one embodiment, the at least one physical variable comprises time, which is provided by a timing unit in the wrist-top computer.

According to one aspect, the invention provides a wrist-top computer firmware product comprising display controlling means adapted to control wrist-top computer display, operation mode controlling means functionally connected to the display controlling means for displaying operation mode-specific information on the wrist-top computer display, means for reading at least one physical parameter provided by the wrist-top computer, and means for storing or accessing variable operation data defining at least part of the operation mode-specific information of at least one operation mode, the variable operation data being stored in a wrist-top computer memory unit, means for applying the variable operation data on the physical parameter for producing operation result forming at least part of the operation mode-specific information of the at least one operation mode.

According to one embodiment, the firmware product comprises software means for changing only the variable operation data in response to communication connection of the product with another software product run on a separate computing unit. The communication connection may be wireless or wired.

The firmware product may be run in a wrist-top computer as described above.

According to one aspect, the invention provides a computer program product for functionalization of a wrist-top computer, the product comprising means for displaying a graphical user interface on a computer display, means for providing a set of physical variables capable of being determined in a wrist-top computer and a set of mathematical operators on the graphical user interface, means for organizing the at least one of the parameters and at least one of the operators as a mathematical formula on the graphical user interface in response to user input through the graphical user interface, means for storing a data structure descriptive of the mathematical formula to a storage device.

Preferably, the storage device is a memory unit of the wrist-top computer. The storing is that case comprises wired or wireless transferring of the data structure directly to the memory unit. However, the data structure may be stored also on an intermediate device such as a personal computer memory device or an internet server memory device, from which it can be further transferred to a wrist-top computer using a suitable link.

According to still another aspect, the invention provides a computerized system for functionalizing wrist-top computers, the system comprising user account management means for maintaining a plurality of user accounts, wrist-top computer operation programming means configured to allow owners of the user accounts to define mathematical operations comprising one or more mathematical operators, one or more physical variables and mutual relations of the operators and variables, storage means for storing the user-defined mathematical operations for the user accounts, means for exporting the user-defined mathematical operations to a wrist-top computer of the owner of the user account or to another external storage device.

The computerized system may be run on an internet server to which the users have access through the internet from their personal computers, handheld devices and/or wrist-top computers, for example.

To cover the various aspects of the invention the terms "mathematical operations", "variable operation data" and "data structure descriptive of a mathematical formula" are used to describe the user-definable portions of the device, software and system covered by the invention. For convenience, these may be commonly called "rules" hereinafter. The functionality of a wrist-top computer to run the rules is called "rule engine".

According to one embodiment, the rules are adapted to comprise data on at least one mathematical operator, at least one physical parameter and instructions on how the mathematical operator is applied on the physical parameter in order to yield the operation result. Typically, the rules comprise information of at least two physical parameters and at least one mathematical operator applied on both of them to yield the operation result. However, more complex operations and formulas may be involved too.

According to one embodiment, the device is adapted to receive new rules as "scripts", i.e. ordered data structures, that it uses to function in a user-defined way. The scripts may be in the form of character, number or binary data, for example. The device interprets and runs the script.

According to one embodiment, the device is adapted to transmit actions made with the rules, i.e. rule results, to an external device where they may be investigated, interpreted, analyzed, processed or shared with other people.

Considerable advantages are obtained the present invention and its embodiments. First of all, the invention provides a dynamic possibility to affect the operation of a wrist-top computer. The device becomes therefore more adaptable and can be utilized in new ways. The functionality of the device is not fixed at the time of purchase and the user has a possibility to configure the device better to meet his or her needs. Also, the manufacturer of the device or third parties may provide new content for the device and transmit, reach, engage and/or affect the users with such new content or other information after purchase.

Embodiments of the invention provide for further advantages. For example, if the rules are kept independent of the firmware of the device, there is no need for software update as new functions are provided or new services are launched. If the device comprises a rule import, functionality features and functionalities of the device can be developed outside of the device and easily taken into use by the user. Further, if the wrist-top computer comprises wireless data transfer capabilities, part of the logic and functionality of the watch may be put in adaptable and transferable scripts, which are manually or automatically loaded into the device from a cloud.

This invention will become more fully understood from the following detailed description, taken in conjunction with the accompanying drawings described herein below, and wherein like reference numerals refer to like parts.

DETAILED DESCRIPTION OF EMBODIMENTS

The invention is now explained using a wrist-top computer and an exemplary device. Most of the features can, however, be used in other portable microcontroller-containing units, such as sensor unit wirelessly connectable to a wrist-top computer.

Wrist-Top Computer

Mechanical and Electronic Units

Figure 1:
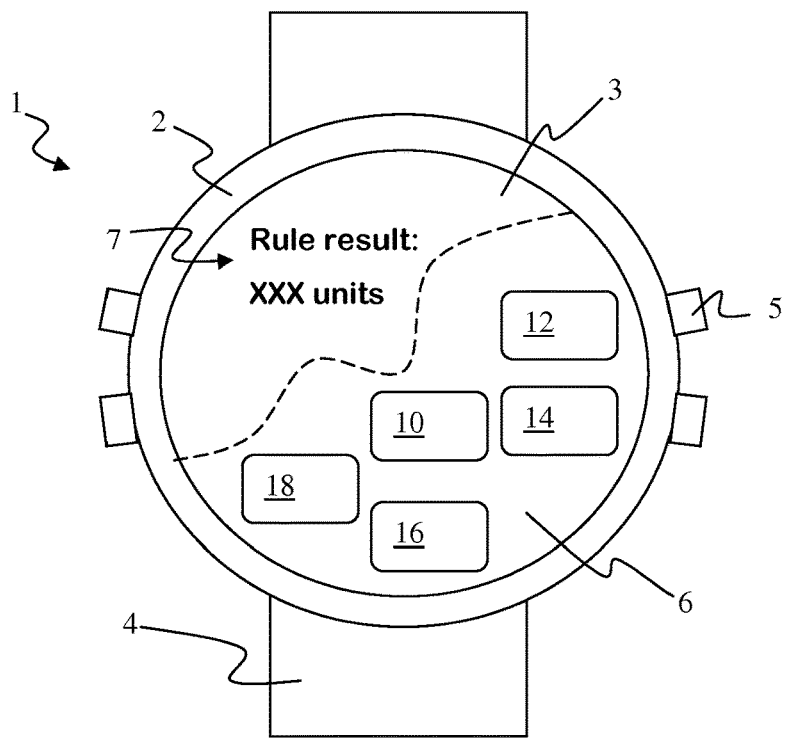
FIG. 1 shows a schematic picture of a wrist-top computer according to one embodiment of the invention.

Starting with the wrist-top computer, FIG. 1 shows a schematic picture of such a device according to one embodiment. The wrist-top computer 1 comprises housing 2 carrying a display 3 and attached to a wristband 4. The device includes user inputs 5, such as buttons as in the exemplary device. In alternative preferred embodiments, other forms of inputs can also be used, such as touch screens, dials, remote transmissions, etc. The display is adapted to show programmed information 7, as will be described later in more detail. The housing 2 encompasses an electronics assembly zone 6 comprising a plurality of the electronic units.

The electronic unit includes a microprocessor 10, a memory unit 12, timing unit 14, sensor or sensor data interface unit 16, and a rule interface mechanism 18 all functionally connected to, or operably engaged with, the microprocessor 10. The timing unit 14 is adapted to provide a time signal, which may be utilized in a clock, timer and/or other timing functions of the device 1. In addition to these units shown in FIG. 1, the device 1 may comprise other separate units, such as a display control unit and various kinds of data transfer or communication units.

Although the memory unit 12 is referred in singular form herein, it may be formed of two or more physical units, as discussed above. For example the firmware and rules and/or results thereof may be stored on different physical memory units, if so desired. According to one example, the firmware is stored in an internal memory of the microcontroller and the rules and/or results in a memory chip external of the microcontroller (e.g. RAM or EEPROM chip), or vice versa.

Physical Variables and Rules

The sensor or data interface unit 16 is configured to provide a measurable physical value, such as an acceleration value, position value, orientation value, pressure value or temperature value, to mention some examples. In one embodiment, the sensor is located in the wrist-top computer, whereby it may be operably coupled with other parts of the device with suitable microcircuits. In another embodiment, the actual sensor in located in an external device and the measurable value physical value is provided to the wrist-top computer through a data interface unit through a preferably wireless data link. Examples of potential sensors, which may be either internal or external, include an acceleration sensor, a velocity sensor, an orientation sensor, a position sensor (e.g. satellite positioning receiver), pressure sensor, magnetic field sensor, temperature sensor and heartbeat or respiration sensor. The device may also utilize both internally and externally measured physical variables at the same time.

The physical variable may be an instant (momentary) variable (e.g. momentary speed) or a derivative variable, such an average (average speed).

Typically, the device is capable of providing two or more physical variables and its software is capable of performing a rule utilizing the two or more physical variables. One of the physical variables may be absolute or relative time obtained using the timer unit 14 and one of the physical variables may be measured internally or externally using a sensor as described above. Alternatively or in addition, two or more internally or externally measured variables may be used. It should be noted that the complexity of the rules, i.e. the number or type of mathematical operators or physical variables, is not limited in any particular way, provided that the computing power of the microprocessor is suitably selected and the rule engine is suitably programmed.

In addition to variable parameters, the device may be configured to utilize one or more constant parameters defined as in a rule and pre-stored in the memory of the device. Examples of constant parameters include age of the user, mass of the user, height of the user, activity class of the user. The constant parameters may comprise also other physiological parameters descriptive of the user or the environment. Constant parameters may also be coded-in in the rules.

It should be noted that the rules can contain also other data in addition to the mathematical formula concerned. Such data may comprise e.g. desired user alarm threshold value(s) associated with the rule, data on the type of alarm (e.g. audible, visual or vibration), or secondary mathematical formulas, such as error calculation formulas associated with the rule.

The rules may be in the form of data structures descriptive of the desired functionality in the form of a script. The scripts are runnable using script-running software, i.e. rule interpreter, such as an ESW-interpreter (debugger), in the wrist-top computer. The scripts may be created using a rule creation tool e.g. in a wrist-top computer, personal computer or web service. Importation or creation and running of the rules will be discussed in later subsections in more detail.

Defining and/or Importing Rules

On the memory unit 12, there is a software, typically the so-called firmware, comprising microprocessor executable instructions for operating various functions of the wrist-top computer. Of specific interest herein is an operation mode which is adapted to run user-specified rules utilizing one or more of the physical variables provided by the sensor or data interface unit 16. In addition, the memory unit 12 comprises a memory portion for storing one or more rules.

The memory portion for storing the rules may be located for example on a RAM or EEPROM unit, external to the microcontroller.

The rule interface mechanism 18 can be provided in the wrist-top computer for allowing the user to change the contents of at least the memory portion 12 in which the rules are defined or which is allocated for the rules. This functionality may be implemented in at least two ways described below.

According to one embodiment, the rule interface mechanism 18 comprises on-device user interface, such as buttons and display or a touch screen, arranged in the wrist-top computer. The software run in the wrist-top computer may in that case comprise a programming mode in which the user may define new rules or modify existing rules by operating the user interface.

According to one embodiment, the rule interface mechanism 18 comprises data transfer units capable of importing rules, which have been defined in an external computing device, such as a personal mobile device or computer or a web server, into the memory portion for the rules.

Running Rules

The software of the device comprises a rule interpreter containing a command set capable of interpreting the instructions contained in the rule data structure. The interpreter may be upgradeable in the device such that the command set may be amended. The command set can thus be chosen to allow running of rules of different complexities.

According to one embodiment, the rule interpreter is built anew in an external device for each rule or rule combination a user wishes to use, and transferred to the device in addition to the rule data structure. This embodiment allows for the memory usage and computing capacity of the device to be optimized.

According to one embodiment, the rule interpreter is an independent software unit from the rules. Thus, the rules may be amended or added without updating the rule interpreter.

According to one embodiment, the interface comprises data transfer units or elements capable of reading and storing the whole firmware, including the rule interpreter and one or more rules, of the device from an external storage or computing device to the memory unit, for changing the user-definable rule(s). Thus, the rule(s) may form an integral part of the firmware of the device, in which case for changing a rule, the whole firmware of the device is updated. Functions of the firmware, other than the rule interpreter are described in a further subsection.

The reception of both rules and interpreter updates, if applicable, can be wireless and take place using a suitable wireless data transfer protocol and related hardware and software.

The rules can be run in one or more operation modes of the wrist-top computer. Running a rule means the physical value(s) defined in the rule are read and the mathematical operation(s) defined in the rule are applied for the physical value(s) to yield a result. The result is shown on the display of the device and/or stored in the memory of the device and/or sent via a data link to another computing device. Running a rule may take place in one or more operation modes of the device. To mention one example, a rule may be run in a timer mode of the wrist-top computer, i.e. during an exercise which the user desires to have timed. Alternatively or in addition, there may be a specific rule-focused operation mode.

According to one embodiment, the device is configured to continuously (including periodically with intervals) run the rule and to update the result of the rule on the display of the device (visual signaling). Alternatively or in addition to that, audible signal(s) may be given depending on the result (audible signaling). In addition or instead of these, any other sensory signaling method, such as vibration, may be used to give feedback of the result to the user. This embodiment allows for flexible monitoring of the result during a sports exercise, for example, in a suitable operation mode of the device.

The rule data structures may contain data on the updating frequency and/or alert signals. Alternatively or in addition to that, they may be defined in the rule-running device.

According to one embodiment, the device in configured to run the rule as an immediate response to use input and to give the result as a visual or audible signal. This embodiment allows for small battery consumption.

According to one embodiment, the wrist-top computer comprises a system, mechanism or element for storing the result of the rule to its memory unit. In a further embodiment, the device comprises a system, mechanism or element for transferring the result of the mathematical operation to an external device using a wired or wireless link. According to one embodiment, not only a single result of the rule is stored and/or transferred, but also its temporal history during a period. The device may comprise an internal log for rule results and/or histories.

According to one embodiment, the memory unit comprises a memory portion for storing a user-definable alphabetical name for the user-definable mathematical operation. This allows for the user to easily distinguish between rules stored in the memory unit.

Firmware

As discussed above, the wrist-top computer is configured to run a firmware product which is stored in its memory unit and adapted to perform the required functions relating to the user-definable rules. As the firmware may be stored and copied independent of the wrist-top computer as a software product, its technical aspects are described in more detail herein.

Figure 2:
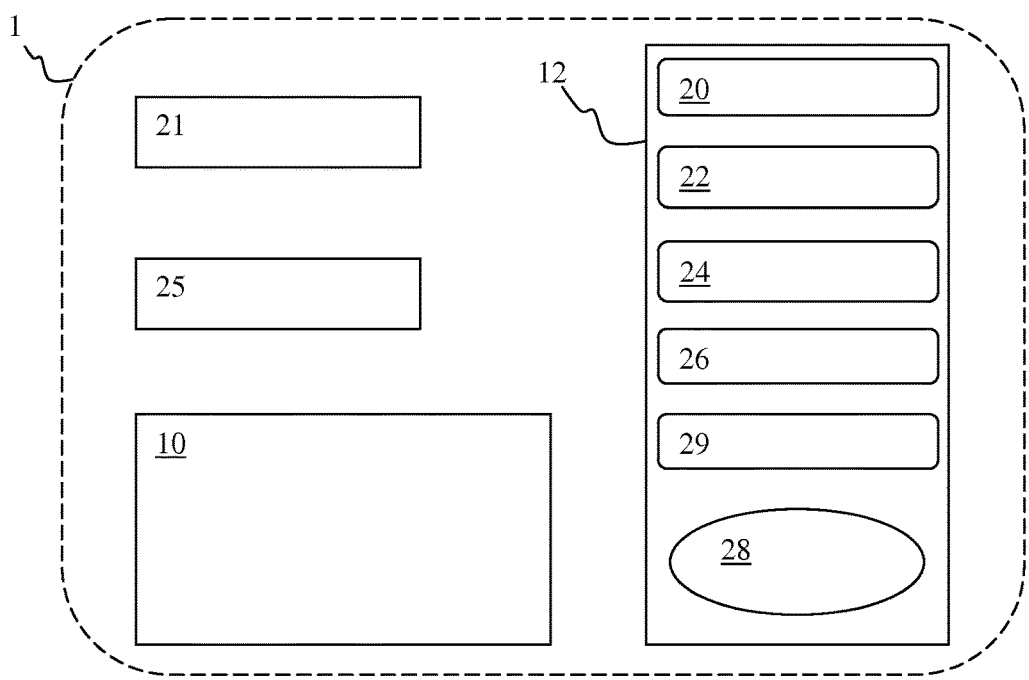
FIG. 2 shows a block diagram of internal hardware and software of a wrist-top computer according to one embodiment of the invention.

With reference to FIG. 2, the firmware—herein shown as being stored on a memory unit 12 of a wrist-top computer 1—comprises display controlling software 20 comprising computer executable instructions for controlling, i.e. showing visual data on a wrist-top computer display 21. In addition, the firmware may comprise operation mode controlling software 22 functionally connected to the display controlling software 20 for displaying operation mode-specific information on the wrist-top computer display 21. There may be several sets of instructions for defining a plurality of operation modes. At least one of the sets comprises instructions for providing user-defined rule data on the display.

In addition, the product comprises parameter reading software 24 which are adapted to read at least one physical parameter provided by sensor or data interface unit 25 of the wrist-top computer. The parameter may be read directly from a sensor unit, data transfer unit, timing unit or memory unit of the wrist-top computer. Typically, at least two different physical parameters are read and utilized, as discussed above.

In addition, the firmware product comprises software 26 for reading rules, i.e., variable operation data defining at least part of the operation mode-specific information a user-definable operation mode, the rules being stored in a rule portion 28 of the wrist-top computer memory unit 12. The product may also comprise a system, mechanism or elements for storing rules defined in the wrist-top computer or in an external computing unit. However, the rule storing function need not be part of the product itself but the rules may be also directly storable to the memory unit 28 when connected to an external computing unit through a cable, for example.

Finally, the firmware product comprises rule applying software 29 (rule interpreter) comprising instructions for applying a rule stored in the memory unit 12 on the actual physical parameter(s) provided during the use of the wrist-top computer from the sensor or data interface unit 25. The result of the rule so applied form at least part of the operation mode-specific information which may be communicated to the user in the at least one user-definable operation mode by suitable signaling mechanism, stored to the memory of the device, and/or sent as a radio message to another computing device.

According to one embodiment, the firmware product comprises a system, mechanism or elements for receiving the variable operation data from an external computing device through data transfer units arranged in the wrist-top computer.

According to one embodiment, the firmware product comprises a system, mechanism or elements for defining the variable operation data in the wrist-top computer 1 through user interface.

The firmware or part of the firmware (e.g. the rule interpreter) may be updateable such that the usage of different sets of parameters, command sets and feedback signaling methods of the result are made available. Thus, the device can be conveniently adapted to the needs of different users or sports.

Connectivity

Figure 3:
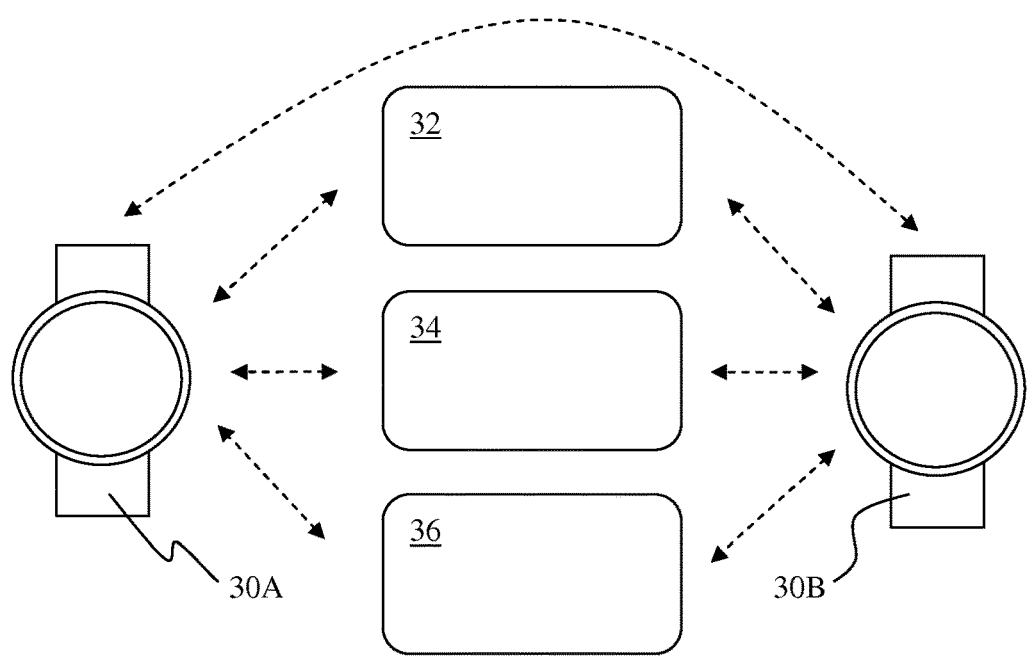
FIG. 3 shows schematically various connectivity options for functionalization of wrist-top computers according to the invention.

With reference to FIG. 3, the functionalization of the wrist-top computer with new rules—in addition or alternatively to through a potential on-device programming mode—may take place through various channels. The same channels are available for the transfer of rule results to another direction.

First, a wrist-top computer 30A may comprise a system, mechanism or elements arranged to provide a direct wired or wireless connection with another wrist-top computer 30B. A Bluetooth link, for example, provides this functionality.

Second, the wrist-top computer 30A may include a wired or wireless data link with an internet server 32.

Third, the wrist-top computer 30A may comprise a wired or wireless data link with a personal computer 34, such as a desktop or laptop computer.

Fourth, the wrist-top computer 30A may comprise a wired or wireless data link with a personal mobile device 36, such as a mobile phone or tablet device.

Suitable standardized data links can include e.g. USB link, Bluetooth link, WLAN link and various cell phone data links.

The various external devices are provided with suitable software and hardware capabilities for allowing transfer or rules and/or rule results through the link concerned.

Computer or Mobile Device Software

According to one aspect, the rules are defined in a computer by the user and transferred to the wrist-top computer using a suitable data link. Therefore, a computer program product for functionalization of a wrist-top computer is provided.

According to one embodiment, the product comprises computer executable instructions for displaying a graphical user interface on a computer display and computer executable instructions for showing a set of physical variables capable of being determined in a wrist-top computer and a set of mathematical operators on the graphical user interface. The graphical user interface comprises interface elements for organizing the parameters and operators as a mathematical formula on the graphical user interface in response to user input. The mathematical formula defines the rule. The user interface may, for example, comprise a first region showing all available physical variables, a second region showing all available operators, and a third region showing the mathematical formula formed by the user. In practice, the user input may be in the form of mouse movements and clicks, touch screen or touchpad gestures and/or keyboard input.

Further, the program comprises computer executable instructions for storing a data structure descriptive of the rule (first data structure) to a storage device. The storage device may be a memory unit or hard disk unit contained in the computer the software is run in. Alternatively or in addition to that, the storage device may be a memory unit of a wrist-top computer or external displayless sensor unit, which is connected to the computer with a data link.

The computer program may be stored and used in an internet server, on a personal computer, or on a personal mobile device. However, it is possible to run the program directly in a wrist-top computer, provided that it has a suitable user interface.

According to one embodiment, the program is adapted to create, in connection with the creation of a new rule, a new rule interpreter and/or command set and/or other piece of software (i.e. a second data structure created by the rule creation program) for the device intended to run the rule. This allows for adapting the device to utilize the information provided by or to the device in the most efficient way and to extend the capabilities of the device by software, when the created piece of software is transferred to the device together with the rule. For example, new sensors, user interface components or algorithms contained in the device may be taken into use by software updates bound to new rules.

According to one embodiment, applying primarily to cases where rules are defined for displayless units, or a unit without a display (such as external sensor units), in wireless connection with a host device (such as a wrist-top computer), the rule creation program is adapted to create a rule interpreter and/or command set and/or other piece of software for both the displayless unit and the host device. For example, a new rule run in the displayless unit can provide new data which can be handled in the host device only by updating parts of its software (i.e. by a third data structure created by the rule creation program) suitably.

Figure 4:
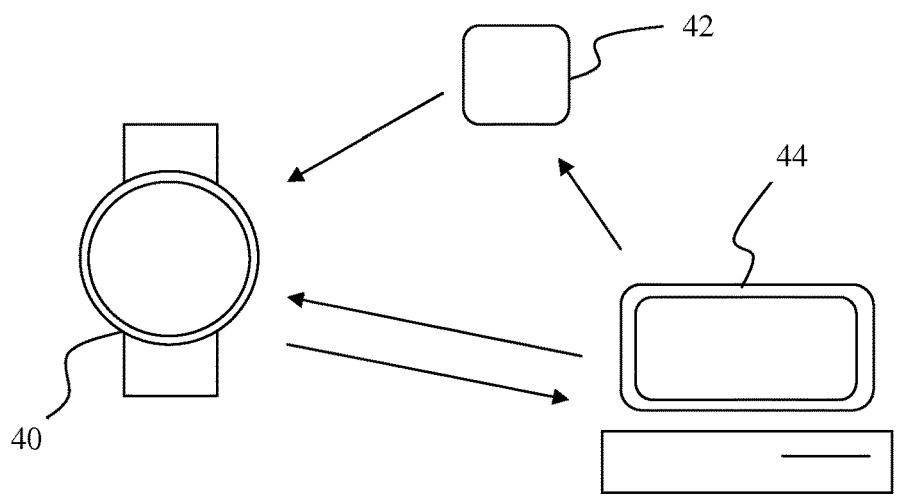
FIG. 4 shows a system according to one embodiment of the invention.

FIG. 4 illustrates the above embodiments. Computer 44 is adapted to run a rule creation software and to create the first and optionally second and/or third data structures, which can be transferred to a wrist-top computer 40 and/or a sensor unit 42 in functional connection with the wrist-top computer 40 so as to achieve the desired functional system capable of running the rule.

Internet System

The present invention may be utilized as part of a computerized social media system. According to one embodiment, the system comprises web server-based user account management allowing for the creation and maintenance of a plurality of user accounts through an internet connection. The system also comprises web server-based graphical wrist-top computer operation programming configured to allow owners of the user accounts to define mathematical operations as described above. The user-defined mathematical operations can be stored on the server and further exported or downloaded to a wrist-top computer of the owner of the user account or to another external storage device.

According to one embodiment, the system comprises software for sharing the user-defined mathematical operations between user accounts.

Further, the system preferably comprises a system or mechanism for receiving data units comprising results of the mathematical operations from the owners of the user accounts, as operated in their wrist-top computers. The transfer of the data units may take place directly from the wrist-top computer to the server through an internet connection or via an external internet-connected computing device, such as a personal computer or mobile device.

Example of a Web Service Including Rules Creating and Sharing Properties

1. Web service members can create rules

Rules can be created by users in the web service with an easy to use tool.

Rules can be shared in the web service community. Additional functions include liking of rules and commenting of rules.

Rules can be created by partners of the device manufacturer or other companies. Branded rules may be highlighted for the users.

Rules can be branded in the web service community.

2. Rules can be browsed/searched in community

Browsing of rules in the service e.g. by sports, most used, most liked, latest.

Sharing of rules into other social media services, to showcase "I made this".

3. Transferred into the wrist-top computer

Any created or selected rule can be transferred from the web service into a wrist-top computer or other portable personal device.

The tool for creating the rules may show variables that can be used from rule enabled device. The set of rules may vary from device to device.

The tool may also show statistics from the whole community that can be used in rules.

Detailed Description of Features of an Exemplary Web Service

The rule creation is carried out in a graphical user interface (GUI), which allows the user to see and select given variables and operations in order to construe rules. Rule construction may be implemented as point-and-click, drag-and-drop or command line-based feature, to mention some possibilities. Any known GUI elements can be used to show the available variables and operations.

A rule using variables XXX and YYY and an operator OPERATOR may be shown as an equation in suitable fields of the GUI:

XXX OPERATOR YYY=RESULT where RESULT is the result of the operation.

RESULT may be used as a variable in a next rule field in order to allow construction of more complex rules. Alternatively or in addition to that, the fields may allow direct construction of more complex rules.

The service may allow testing of the rule in the GUI using test values of the variables so that the user can see if the rules is working properly.

There may also be a field which allows the user to give a name for the rule or the end result or any intermediate result thereof.

When the rule is ready in the GUI, it is converted into a script or other machine-readable code, such as a number or binary code.

The rule code can then be transferred to a wrist-top computer comprising a suitable interpreter software for running the code.

Rule Examples

Show during exercise, how many chocolate bars you have burnt:
Rule: Calories/490.65 kcal=Result chocolate bars
Calculate the total distance while running on a 400 m running track, by pushing lap button after each lap
Rule: Lap count*400 m=Result m
Measure the slope grade of the hill, by pushing lap button when the hill starts
Rule: Lap Altitude/Lap Distance*100=Result %
Estimate power output in Watts based on speed and grade:
Rule: Lap Altitude/Lap Distance*speed m/s*weight*9.8 m/s$^2$=Result Watts While the preferred embodiments of the invention have been illustrated and described, it will be appreciated that various changes can be made therein without departing from the spirit and scope of the invention. One of skill in the art will understand that the invention may also be practiced without many of the details described above. Accordingly, it will be intended to include all such alternatives, modifications and variations set forth within the spirit and scope of the appended claims. Further, some well-known structures or functions may not be shown or described in detail because such structures or functions would be known to one skilled in the art. Unless a term is specifically and overtly defined in this specification, the terminology used in the present specification is intended to be interpreted in its broadest reasonable manner, even though may be used conjunction with the description of certain specific embodiments of the present invention.

What is claimed is:

1. A portable microcontroller-operated wrist-top computer system for a user comprising:
   a wrist-top computer including,
      a housing;
      a wristband coupled to the housing;
      a memory within the housing;
      a microcontroller including software stored on the memory;
      at least one sensor providing at least one physical variable, wherein the software is adapted to read the physical variable using the at least one sensor and to perform a mathematical operation utilizing the physical variable;
      a rule interface mechanism configured to enable the user to change the contents of a set of rules within the memory; and
      a rule interpreter including a command set capable of interpreting the instructions contained in the set of rules; and
   an interface adapted to allow defining of the mathematical operation in the memory by the user of the wrist-top computer.

2. The portable microcontroller-operated computing wrist-top computer system of claim 1, further comprising a displayless unit including a mechanism for wirelessly transmitting the result of the mathematical operation utilizing the physical variable to the wrist-top computer.

3. The portable microcontroller-operated computing wrist-top computer system of claim 1, wherein the memory includes a memory unit integrated on a single chip with the microcontroller, and wherein at least one of the software and the mathematical operation is stored on the integrated memory unit.

4. The portable microcontroller-operated computing wrist-top computer system of claim 1, wherein the memory includes a memory unit external to the microcontroller and, wherein at least one of the software and the mathematical operation is stored on the external memory unit.

5. The portable microcontroller-operated computing wrist-top computer system of claim 1, wherein the mathematical operation and information on the physical variable are contained in a variable data structure on the memory, wherein the data structure is writable through the interface, and wherein the software comprises an interpreter for reading the data structure and for running the mathematical operation defined in the data structure in the device, and, optionally, for displaying or storing the result of the mathematical operation to the memory.

6. The portable microcontroller-operated computing wrist-top computer system of claim 1, wherein the interface is functionally coupled to the memory for changing a part of the memory defining the mathematical operation.

7. The portable microcontroller-operated computing wrist-top computer system of claim 1, wherein the interface includes a user interface arranged in the wrist-top computer.

8. The portable microcontroller-operated computing wrist-top computer system of claim 1, wherein the interface includes a data transfer mechanism for importing a mathematical operation, which has been defined in an external computing device, the external computing device being selected from the group consisting of a personal mobile device, a computer and a web server, into the memory for storing the user-definable mathematical operation.

9. The portable microcontroller-operated computing wrist-top computer system of claim 1, wherein the mathematical operation is part of the software and, wherein the interface includes data transfer mechanism for updating the whole software from an external computing device, for storing the user-definable mathematical operation.

10. The portable microcontroller-operated computing wrist-top computer system of claim 1, wherein the at least one physical variable is selected from the group consisting of, time, velocity, position, direction, orientation, and a combination thereof.

11. The portable microcontroller-operated computing wrist-top computer system of claim 1, wherein the at least one sensor is adapted to measure the at least one physical variable.

12. The portable microcontroller-operated computing wrist-top computer system of claim 1, wherein the at least one sensor is adapted to receive the at least one physical variable from an external measurement unit.

13. The portable microcontroller-operated computing wrist-top computer system of claim 1, further including a mechanism for storing the result of the mathematical operation and/or transferring the result of the mathematical operation to an external device.

14. The portable microcontroller-operated computing wrist-top computer system of claim 1, further including a display and a system for displaying and continuously updating the result of the user-defined mathematical operation on the display.

15. The portable microcontroller-operated computing wrist-top computer system of claim 1, wherein the at least one sensor provides at least two variable parameters and, wherein the software performs a mathematical operation utilizing the at least two variable parameters.

16. The portable microcontroller-operated computing wrist-top computer system of claim 1, wherein the memory includes a memory portion for storing a user-definable alphabetical name for the user-definable mathematical operation.

17. A wrist-top computer firmware product for a user, comprising:
a display controller adapted to control a wrist-top computer display;
an operational mode controller functionally connected to the display controller for displaying operational mode-specific information on the wrist-top computer display;
at least one sensor for reading at least one physical parameter of the user;
memory including one or more constant parameters of the user and variable operation data defining at least part of the operational mode-specific information of at least one operation mode; and
a microcontroller applying the variable operation data on the physical parameter for producing an operational result including at least part of the operational mode-specific info nation of the at least one operational mode.

18. The wrist-top computer firmware product according to claim 17, wherein the variable operation data is adapted to comprise data on at least one mathematical operator, at least one physical parameter and instructions on how the mathematical operator is applied on the physical parameter in order to yield the operation result.

19. The wrist-top computer firmware product according to claim 17, further including means for receiving the variable operation data from an external computing device through data transfer means arranged in the wrist-top computer.

20. The wrist-top computer firmware product according to claim 17, further including means for defining the variable operation data in the wrist-top computer through user interface means.

21. The wrist-top computer firmware product according to claim 17, wherein the firmware product is stored in a wrist-top computer memory unit.

22. The wrist-top computer firmware product according to claim 17, further including a command set for interpreting data structures comprising the variable operation data in order to be able to obtain the operation result.

23. A computerized system for functionalizing wrist-top computers, comprising:
a user account management system configured for maintaining a plurality of user accounts;
a wrist-top computer operation programming mechanism configured to allow owners of the user accounts to define mathematical operations comprising one or more mathematical operators, one or more physiological variables of the users and mutual relations of the operators and variables, the wrist-top computer operation programming mechanism configured to utilize one or more constant physiological parameters of the users;
a memory for storing the user-defined mathematical operations for the user accounts,
a communication link for exporting the user-defined mathematical operations to a wrist-top computer of the owner of the user account or to an external storage device.

24. The system of claim 23, further including a mechanism for sharing the user-defined mathematical operations between user accounts.

25. The system of claim 23, further including a mechanism for receiving data units comprising results of the mathematical operations from the owners of the user accounts, as operated in their wrist-top computers.

26. The portable microcontroller-operated computing wrist-top computer system of claim 1, wherein the at least one physical variable is selected from the group consisting of, altitude, depth, barometric pressure, and temperature.

27. The portable microcontroller-operated computing wrist-top computer system of claim 1, wherein the at least one physical variable is a physiological variable measured from the user, and wherein the physiological variable is heartbeat frequency, respiration frequency or a combination thereof.

* * * * *